United States Patent [19]
Komatsu

[11] Patent Number: 6,097,483
[45] Date of Patent: Aug. 1, 2000

[54] IMAGE DETECTION APPARATUS

[75] Inventor: Koichiro Komatsu, Tokyo, Japan

[73] Assignee: Nikon Corporation, Tokyo, Japan

[21] Appl. No.: 09/259,733

[22] Filed: Mar. 1, 1999

[30] Foreign Application Priority Data

Feb. 27, 1998 [JP] Japan .................................. 10-047855
Feb. 22, 1999 [JP] Japan .................................. 11-042714

[51] Int. Cl.[7] .................................................. G01N 21/00
[52] U.S. Cl. .................................... 356/237.2; 356/237.4; 356/237.5
[58] Field of Search ................................... 356/375, 376, 356/371, 400, 237.1, 237.2, 237.3, 237.4, 237.5, 399, 401, 139.1, 239.7, 239.8; 250/559.37

[56] References Cited

U.S. PATENT DOCUMENTS

| | | | |
|---|---|---|---|
| 5,218,415 | 6/1993 | Kawashima ............................... | 356/375 |
| 5,510,892 | 4/1996 | Mizutani et al. ........................ | 356/375 |
| 5,535,005 | 7/1996 | Mukherjee-Roy et al. ............. | 356/371 |
| 5,587,794 | 12/1996 | Mizutani et al. ........................ | 356/375 |

*Primary Examiner*—Hoa Q. Pham

[57] ABSTRACT

An image detection apparatus (10) having an illumination system (IS) irradiates light onto the surface (30S) of an object 30 to be inspected for defects. A detection optical system (34) condenses the light from the surface and forms an image of the surface on an image detector (48). The detection optical system includes a receiving mirror (38) having an optical axis ($A_{38}$) that intersects the reference optical axis ($A_{34}$) of the detection optical system. A processing apparatus (60) includes a processing system (62) that performs image processing based on an output from the detector corresponding to the image. The processing system includes an image distortion correction unit (62a) for eliminating the effects of distortion in the image of the surface generated by the inclination of the surface with respect to the reference optical axis and the receiving mirror.

17 Claims, 4 Drawing Sheets

IMAGE DETECTION APPARATUS

FIELD OF THE INVENTION

The present invention relates to an image detection apparatus, and in particular to such apparatus suitable for the inspection of the surface of substrates such as wafers and liquid crystal substrates used in manufacturing semiconductor devices and liquid crystal displays.

BACKGROUND OF THE INVENTION

Conventionally, inspection of wafers and liquid crystal display substrates (hereinafter, collectively "substrates") is performed by an inspector who directly holds a substrate in relation to a point light source. The inspector then attempts to visually detect defects such as scratches, foreign matter, unevenness in the coating of resist and abnormalities in the transfer pattern of the substrate surface. Among such defects, some are observed while others are not observed, depending on the direction of the rays incident the substrate, and the direction of the line of sight of the inspector. Consequently, the inspection of defects is performed by rotating and inclining the substrate relative to the light source. However, foreign matter like sweat and dirt may adhere to the substrate being inspected because it is directly handled by the inspector. Thus, inspection apparatus have been proposed wherein the substrate to be inspected is suction-clamped to a holder capable of rotating and inclining the substrate under observation. This allows the inspector to observe the substrate without direct contact.

Inspection apparatus have been proposed wherein the shape of the light source for irradiating the substrate surface is planar or linear, making the defects easier to see. However, this type of sensory inspection ultimately depends on the vision of the inspector. Thus, the inspection criteria vary with the inspector's skill, level of fatigue and other subjective factors. This makes it difficult to consistently perform substrate inspection based on a fixed (i.e., objective) standard.

To solve the abovementioned problems, inspection apparatus have been proposed that aim to stabilize the inspection standard by automating the inspection of the substrate surface using image processing.

Briefly, in image processing apparatus for substrate inspection, a nearly parallel illumination irradiates the substrate surface from a predetermined direction. Specularly reflected light, diffracted light from the surface pattern, and scattered light from foreign matter, scratches, etc., on the substrate surface are condensed by a concave mirror. An imaging lens, as a light receiving optical system, forms an image of the substrate which is photoelectrically detected by an image detector, such as a CCD. The image detector then outputs an image signal to an image processing system, which detects unevenness in the coating on the substrate, abnormalities in the transfer pattern arising from defocusing when transferring a pattern (e.g., a mask pattern) onto the substrate, and scratches, as well as the presence of foreign matter on the substrate surface. This is accomplished by comparing the image signal from the image detector to information related to a previously stored normal, (i.e., reference) substrate surface image.

When starting up a manufacturing line for manufacturing semiconductor devices or liquid crystal displays, it is difficult to properly transfer the patterns onto the substrates. It is also difficult to form normal patterns over the entire substrate surface because of instabilities in the manufacturing process. Consequently, there is no choice but to detect defects of such substrates automatically by image processing. To perform feature extraction of defects by image processing, algorithms that recognize periodic structures as non-defects are often employed.

Preferably, the detection optical system in the inspection apparatus includes a concave mirror for condensing light from the substrate surface, and a light receiving optical system (e.g., an imaging lens) for guiding the condensed light to the image detector. To prevent the substrate from being in shadow, an off-axis construction is typically adopted so that the central axis (i.e., the optical axis of the detection optical system) through which the center of the light beam from the substrate passes, and the optical axis of the concave mirror form a predetermined angle. In this way, the imaging lens does not overlap the substrate.

However, if this type of off-axis construction is adopted, the image of the substrate surface formed on the light receiving surface of the image detector is distorted. Thus, if image processing is performed as is, such distortion may cause a false detection.

In addition, the detection optical system does not necessarily capture only the light beams proceeding in a direction perpendicular to the substrate surface (i.e., the substrate surface normal) when it receives specularly reflected light and diffracted light from the surface. Thus, the substrate surface image formed on the image detector becomes a tilted image. This compresses the image in the tilted direction. Consequently, if the tilted image is image processed after photoelectric detection by the image detector, false detection occurs.

There is also the problem that the compression ratio of the tilted image is not fixed. When the detection optical system receives diffracted light from the substrate surface, the tilt angle changes due to the pitch of the pattern formed on the substrate.

SUMMARY OF THE INVENTION

The present invention relates to an image detection apparatus, and in particular to such apparatus suitable for the inspection of the surface of substrates such as wafers and a liquid crystal substrates used in manufacturing semiconductor devices and liquid crystal displays.

The present invention solves the abovementioned problems. In particular, it has the objective to provide an image detection apparatus capable of eliminating the effects of image distortion due to inclination of the surface of a substrate being inspected, with respect to the optical axis of the detection optical system. By the off-axis construction, the present invention can perform high-precision defect detection.

As described in greater detail below, in the apparatus of the present invention, the effects of distortion of the image of the substrate surface due to the off-axis arrangement of the receiving mirror (concave mirror) in the detection optical system and the substrate's orientation with respect to the optical axis of the detection optical system can be eliminated. In particular, the inspection apparatus is capable of performing stable inspection with high accuracy and high efficiency in detecting defects. These defects include abnormalities, foreign matter, scratches in the pattern on the surface, and unevenness in the coating of resist and/or other layers on the substrate.

Accordingly, a first aspect of the invention is an image detection apparatus for detecting defects of a surface having a surface normal. The apparatus comprises an illumination system designed so as to obliquely illuminate the surface.

The apparatus further includes a detection optical system having a first axis forming a first angle with the surface normal, and a second axis forming a second angle with the first axis. The detection optical system is designed so as to receive light from the surface substantially along the first axis and to form an image of the surface along a third axis. The image so-formed includes an amount of distortion which depends on the first and second angles. The system further includes a photoelectric detector arranged along the third axis. The photoelectric detector photoelectrically detects the image, including the amount of distortion therein. The photoelectric detector is electrically connected to an image distortion correction unit. The latter is designed so as to substantially eliminate the amount of distortion in the image based on the first and second angles, thereby forming a substantially distortion-free image. The apparatus further includes a tilt stage capable of holding the object and maintaining the surface at an inclination with respect to at least one of first and second axes and an inclination detection apparatus in communication with the tilt stage. The inclination detection apparatus is designed to detect the inclination and to provide an output signal corresponding to the inclination.

A second aspect of the invention is the apparatus described above, wherein the detection optical system includes a receiving optical system.

A third aspect of the invention is a method of forming a substantially distortion-free image of a surface having a surface normal. The method facilitates inspecting defects on the surface and comprises the steps of first, obliquely illuminating the surface. The next step is receiving light from the surface using a detection optical system having a first optical axis which forms a first angle with respect to the surface normal. The next step is forming a first image of the surface along a second optical axis which forms a second angle with the first axis. The image has an amount of distortion corresponding to at least one of the first and second angles. The next step is determining the amount of distortion in the image based on at least one of the first and second angles. The final step is removing the amount of distortion, as determined in the previous step, from the image, thereby forming a substantially distortion-free image.

A fourth aspect of the invention is the method, as described immediately above, and further includes the step, after the final step of creating a substantially distortion-free image, of inspecting surface defects in the substantially distortion-free image.

DETAILED DESCRIPTION OF THE INVENTION

The present invention relates to an image detection apparatus, and in particular to such apparatus suitable for the inspection of the surface of substrates such as wafers and a liquid crystal substrates used in manufacturing semiconductor devices and liquid crystal displays.

Figure 1:
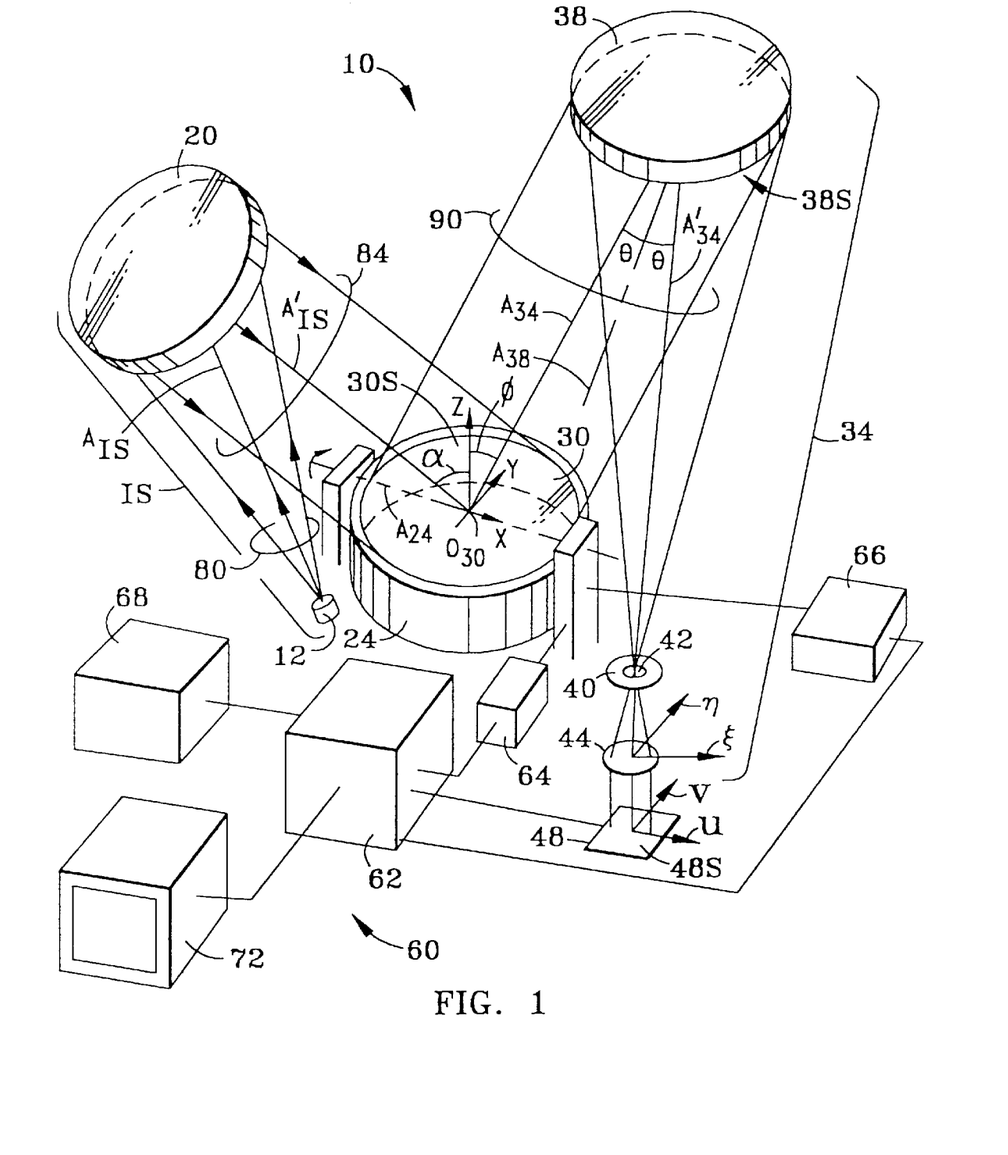
FIG. 1 is a schematic diagram the surface inspection apparatus according to the present invention.

With reference to FIG. 1, surface defect detection apparatus 10 detects defects in or on a substrate surface (e.g, a wafer surface, a liquid crystal display surface, or the like). By obliquely illuminating the substrate surface, specularly reflected light, diffracted light and scattered light are generated, the latter being due primarily to defects present in or on the surface. Accordingly, apparatus 10 achieves inspection of abnormalities of, for example, the resist pattern on a wafer surface and abnormalities in the shape of the pattern formed on the wafer. This is accomplished by photoelectrically detecting diffracted light from the wafer surface. In addition, the inspection of foreign matter like dirt on the substrate surface and scratches on the substrate surface is achieved by photoelectrically detecting scattered light from the substrate surface. The inspection of unevenness in a coating on the substrate surface (e.g., resist formed on the wafer surface and the resist thickness unevenness) is achieved by photoelectrically detecting specularly reflected light or diffracted light from the substrate surface. The inspection of defects of the substrate surface itself is achieved by photoelectrically detecting specularly reflected light from the substrate surface.

Abnormalities of the resist pattern, in the pattern formed on the substrate surface, foreign matter like dirt on the wafer surface, surface scratches, unevenness of the resist coating (i.e., resist thickness unevenness) formed on the substrate surface, and defects of the substrate surface itself that occur when forming a circuit and the like during manufacturing of an IC, liquid crystal substrate or the like are generically and collectively referred to herein as "defects."

With continuing reference to FIG. 1, apparatus 10 comprises a light source 12 which is preferably a point source, or nearly so. A concave mirror 20 is arranged adjacent light source 12 such that its focal point position substantially coincides with the position of the light source. In this arrangement, concave mirror 20 serves as a receiving mirror, as described below. Light source 12 and concave mirror 20 constitute an illumination system IS having an optical axes $A_{IS}$ and $A'_{IS}$. Apparatus 10 further includes a tilt stage 24 capable of supporting a substrate 30 having a surface 30S. Tilt stage 24 is tiltable about a rotation axis $A_{24}$.

In apparatus 10, an X-Y-Z coordinate system is employed, wherein the origin is the center of surface 30S, the X-axis is the direction parallel to rotation axis $A_{24}$ of tilt stage 24, the Y-axis is the direction perpendicular to rotation axis $A_{24}$, and the Z-axis is normal to surface 30S in a state wherein tilt stage 24 is level.

Adjacent tilt stage 24 is detection optical system 34 with a reference optical axis $A_{34}$ and a concave mirror 38 serving as an exemplary receiving optical system. Concave mirror 38 includes an optical axis $A_{38}$ and a reflective surface 38S. Axes $A_{34}$ and $A_{38}$ intersect at a predetermined angle θ. Concave mirror 38 is set off-axis in the direction (X-direction) orthogonal to the plane in which the normal to surface 30S is inclined (i.e., the Y-Z plane orthogonal to rotation axis $A_{24}$). Detection optical system 34 further includes an aperture stop 40 having a circular opening 42 and is arranged substantially at the focal point position of concave mirror 38 and in the vicinity of rotation axis $A_{24}$. Downstream from aperture stop 40 is an imaging lens 44, which serves as a light receiving optical system. The plane that includes optical axis $A_{38}$ and optical axis $A_{34}$ and that exists between the center of substrate surface 30S and concave mirror 38 and optical axis $A_{34}$ that exists between concave mirror 38 and imaging lens 44 traverses the X-axis at an angle φ with respect to normal (i.e., Z-direction) of substrate 30S.

With continuing reference to FIG. 1, adjacent imaging lens 44 is an image detector 48, which may be a photoelectric detector such as a CCD. Image detector 48 includes a light receiving surface 48S arranged such that it nearly coincides with the rear focal point position of imaging lens 44, and such that it is nearly optically conjugate with surface 30S.

Apparatus 10 further includes a processing apparatus 60 comprising a processing system 62 electrically connected to image detector 48, a drive apparatus 64 electrically connected to the processing system and in operative communication with tilt stage 24 for driving the tilt stage, an inclination detection apparatus 66 in communication with tilt stage 28 for detecting the inclination of the tilt stage, an input unit 68 such as a console, electrically connected to the processing system, and a display apparatus 72 electrically connected to the processing system. Processing apparatus 60 is discussed in more detail below.

With continuing reference to FIG. 1, the off-axis angle θ of concave mirror 38 and the inclination angle (or, tilt angle) φ of substrate 30 are orthogonal in apparatus 10. Thus, the direction of the distortion in the image or substrate surface 30S due to the off-axis angle of concave mirror 38 and the inclination of substrate 30 can be made orthogonal on image detector 48. This greatly simplifies the correction of distortion, as discussed below.

With continuing reference to FIG. 1, the operation of apparatus 10 is now described. Light source 12 supplies a light beam 80 having a predetermined wavelength. Because light source 12 is a point source (or nearly so), light beam 80 is divergent. Concave mirror 20 condenses light beam 80 to form a nearly parallel light beam 84 which is directed toward surface 30S of substrate 30. Light beam 84 obliquely irradiates surface 30S along optical axis $A'_{IS}$ from a predetermined inclination direction, namely a predetermined incident angle α.

Light beam 84 diffracts from surface 30S. The $n^{th}$ order diffraction angle $\phi_n$ of the diffracted light is expressed by equation (1), below. In equation (1), ρ is the pitch of the pattern (not shown) formed on surface 30S, λ is the wavelength of the illumination light, n is an integer, $\phi_n$ indicates the angle of reflection for the $n^{th}$ detraction order (specularly reflected light when n is 0) and $\phi_i$ is the incident angle:

$$\sin \phi_n - \sin \phi_i = n\lambda/p \quad (1)$$

Tilt stage 24 is capable of tilting substrate surface 30S by predetermined angle φ so that light specularly reflected, diffracted or scattered therefrom satisfies equation (1), and is guided to and collected by detection optical system 34. Tilt stage 24 may also be tilted by a predetermined amount by drive apparatus 64 about rotation axis $A_{24}$.

Figure 2:
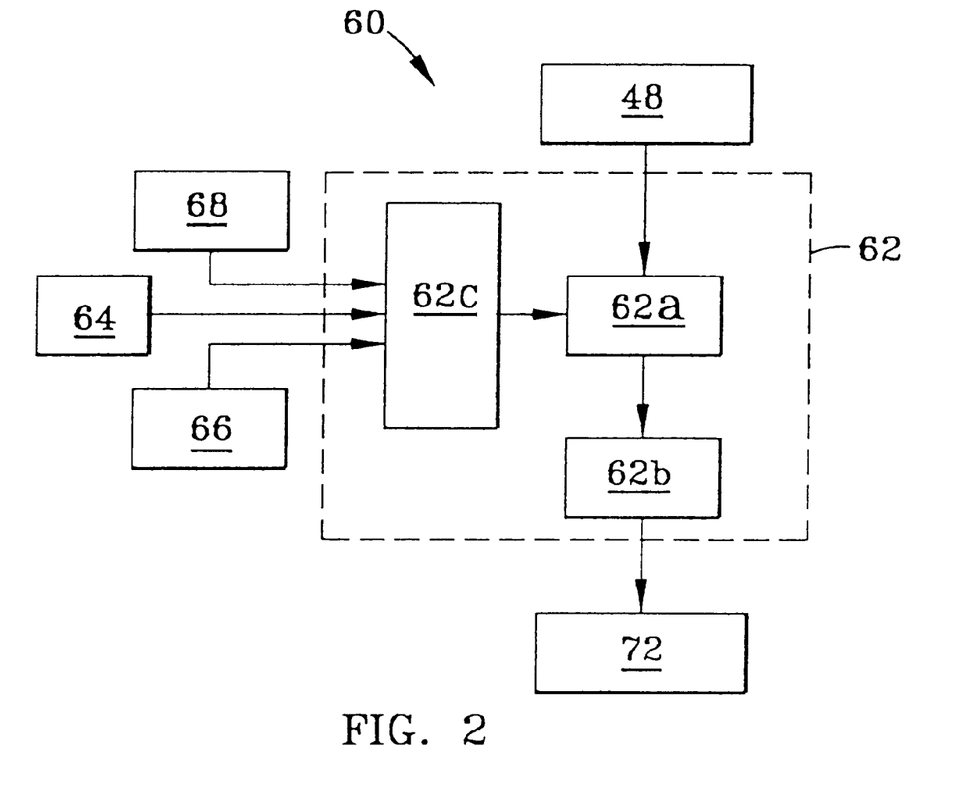
FIG. 2 is a schematic diagram of the configuration of the processing system of the surface inspection apparatus shown in FIG. 1.

With reference now also to FIG. 2, the amount of inclination of tilt stage 24 is detected by inclination detection apparatus 66. Drive apparatus 64 is controlled by a control unit 62c electrically connected thereto within processing system 62. An output signal corresponding to the amount of inclination of tilt stage 24 (i.e., the inclination amount of surface 30S) detected by inclination detection apparatus 66 is input to an image distortion correction unit 62a inside processing system 62 via control unit 62c, which is electrically connected to the image distortion correction unit. A light beam 90 comprising specularly reflected light, diffracted light and/or scattered light from surface 30S is condensed onto aperture stop 40 by the condensing action of concave mirror 38. This light passes through circular opening 42, and is subsequently imaged by imaging lens 44 onto surface 48S of image detector 48. The image formed on surface 48S is that of surface 30S of substrate 30.

The output signal that includes the information pertaining to the image formed on image detector surface 48S and the output signal from inclination detection apparatus 66 related to the inclination of surface 30S are input to image distortion correction unit (image distortion correction system) 62a (FIG. 2). Image distortion correction unit 62a takes into consideration the inclination of surface 30S with respect to optical axis $A_{34}$ and the image of surface 30S distorted by the off-axis angle of receiving mirror 38.

With continuing reference to FIG. 2, processing apparatus 60 is now discussed in greater detail. As discussed above, to detect defects on surface 30S of substrate 30, information, such as the amount of inclination of tilt stage 24, is input into control unit 62c via input unit 68. Input unit 68 may be a computer console or control data file reading mechanism. Control unit 62c tilts tilt stage 24 via drive apparatus 64. The amount of inclination of tilt stage 24 is detected by inclination detection apparatus 66. This inclination information is input into control unit 62c and is used for feedback control so that tilt stage 24 is inclined by a predetermined amount. In so doing, substrate surface 30S is then irradiated by light beam 84 from light irradiation system IS. Light in light beam 84 is then specularly reflected, diffracted, and/or scattered from surface 30S. This image light is detected by detection optical system 34 and forms an image (not shown) of surface 30S on image detector surface 48S. This is photoelectrically converted by image detector 48 and the output signal therefrom is input into image distortion correction unit 62a. Simultaneously, the signal from inclination detection apparatus 66 corresponding to the amount of inclination of tilt stage 24 is input into image distortion correction unit 62a indirectly via control unit 62c. Image distortion correction unit 62a performs a predetermined computation based on the information from inclination detection apparatus 66 and the information from image detector 48. This computation derives the amount of distortion of the image of surface 30S from the inclination of the surface with respect to optical axis $A_{34}$ of detection optical system 34. In other words, the computation uses at least one of angles φ and θ. Correction unit 62a then corrects the distorted image of surface 30S and outputs an image-corrected signal containing information corresponding to the corrected image.

The information pertaining to the image corrected by image distortion correction unit 62a is input via the image-corrected output signal to image processing unit 62b electronically connected thereto. The latter performs feature identification and extraction of the defects from the image information, and detects abnormalities in the pattern on surface 30S, as well as other defects. For wafers manufactured for memory and the like, a plurality of circuit elements is printed by repeatedly exposing a single exposure field using, for example, a step-and-repeat exposure apparatus (i.e., a stepper). This results in the same pattern being repetitively transferred onto the wafer, thereby forming a global periodic exposure pattern. In contrast, pattern abnormalities due to defocusing, as well as defects, scratches, foreign matter and the like (discussed further below), differ from the global periodic exposure pattern, and are observed locally. Such local changes are detected as defect features. Defects detected by image processing unit 62b are tabulated for each wafer. If the number of detected defects or the aggregate surface area exceeds a predetermined value, the wafer in question is judged to be defective. In addition, an image of the wafer can also be displayed and observed by an operator on display apparatus 72 as the need arises. For example, the operator may need to verify that diffracted light is entering detection optical system 34 when setting the inspection conditions.

Defective wafers can be screened based on defect data tabulated for each wafer. After a wafer is inspected, it is unloaded from tilt stage 24 (FIG. 1) and is stored in a wafer storage unit (not shown), such as a storage cassette. At this point, a number of storage cassettes are prepared, some of which are assigned to store conforming wafers that proceed to the next process. Other storage cassettes are assigned to store defective (i.e., non-conforming) wafers. Determining in which cassette a wafer should be stored is made based on information from image processing unit 62b as to whether the wafer is a conforming wafer or a defective wafer.

For example, a wafer can be inspected after developing the resist thereon. If the wafer is found to be non-conforming, the wafer can be "reworked." This involves stripping the resist from the wafer, re-coating the wafer with resist, and then re-exposing the newly coated wafer. Thus, even if a wafer is judged to be defective, it can be reworked to form a conforming wafer without the need to discard it, thereby improving product yield.

By using the above-described automatic inspection process as an automatic screening process, the need for the wafers to be manually handled is minimized. As manual handling is the principal cause of introducing undesirable foreign matter to the wafer, the amount and frequency of such matter adhering to the wafers is also reduced. To further reduce the need for human contact with the wafers, monitoring of the wafers can be performed by isolating display apparatus 72 from the rest of apparatus 10.

In the present invention, observed defects have features which can be inspected with their causes. Accordingly, the defects can be classified according to these features. Representative defects include: a) defocus defects that appear as concentric circular rings due to the wafer being vacuum-chucked and exposed with foreign matter adhering to the surface; b) unevenness defects arising from unevenness in the resist film thickness due to a coater defect (i.e., a defect in the device which deposits the resist film on the wafer), which are detected as radial-shaped unevenness; and b) comet-shaped defects caused by part of the resist film being absent or thinned due to the resist being coated with foreign matter adhering to the wafer.

Accordingly, inspection results can be tabulated based on the above classification. These results might be, for instance, the defect position and defect type in each process and each wafer. Then, the correlation of this information with the occurrence of defective products is calculated. This allows for the cause of defective wafers to be inspected. Further, settings can also be made so that the standard for judging a defective wafer is optimized according to the type of wafer, and so that certain types of defects that do not affect product performance can be ignored.

Figure 3:
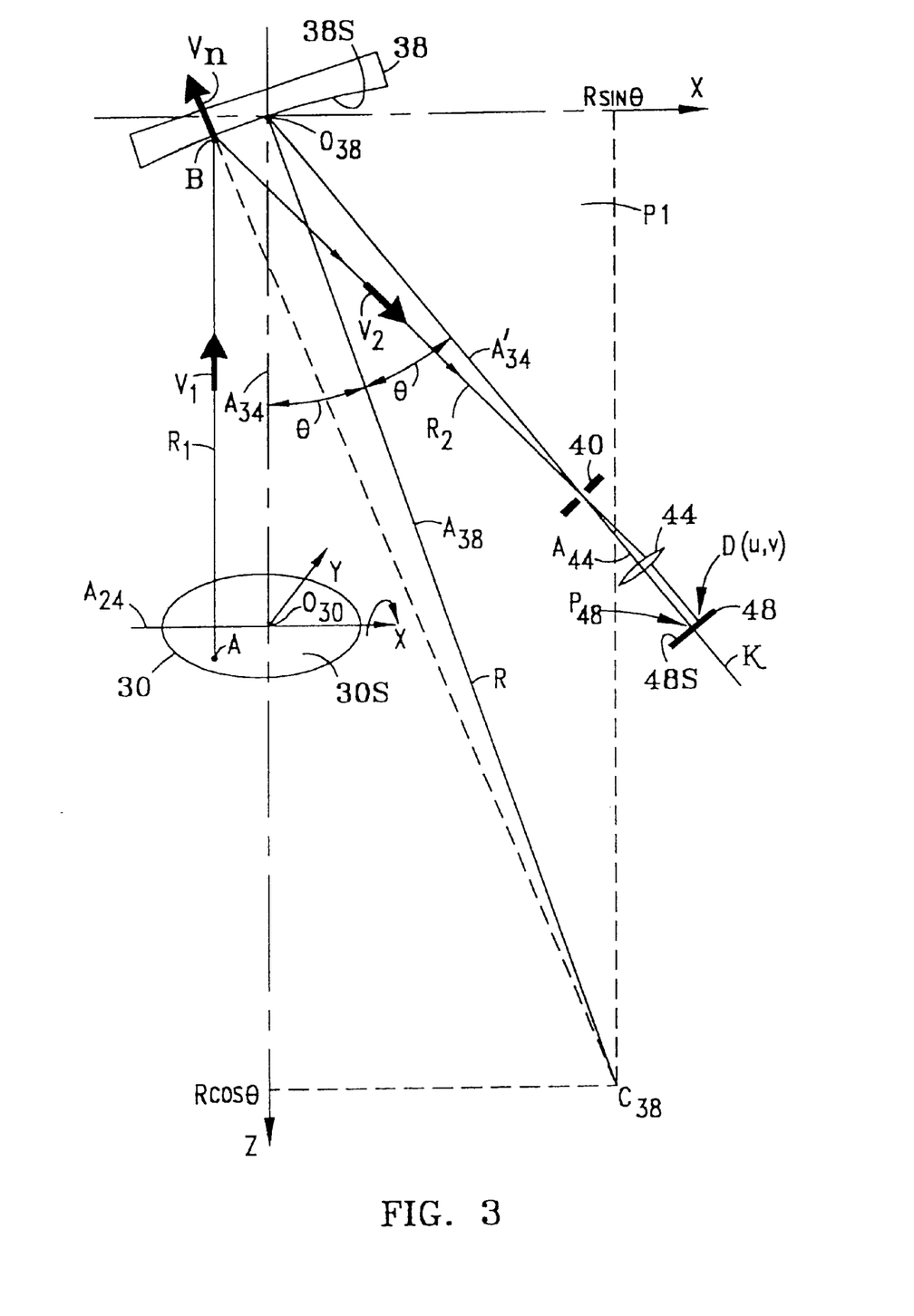
FIG. 3 is a close-up schematic view of the surface inspection apparatus of FIG. 1 showing the beam geometry associated with the second concave mirror.

Eliminating the effects of image distortion using image distortion correction unit 62a is now explained. With reference to FIG. 3, apparatus 10 includes a plane P1 defined by optical axis $A_{34}$ of detection optical system 34 and optical axis $A_{38}$ of concave mirror 38. Plane P1 traverses the X-axis at an angle of $\phi$ with respect to the normal of surface 30S.

As shown in FIG. 3, a light ray $R_1$ with a unit vector $V_1$ in the propagation direction thereof represents light that is either reflected, diffracted or scattered from a point A on surface 30S. Ray $R_1$ proceeds toward concave mirror 38 of detection optical system 34 and is reflected at a point B on surface 38S of the concave mirror to form a light ray $R_2$ with unit vector $V_2$ in the propagation direction thereof. Concave mirror 38 includes a surface normal $V_n$ at point B. In this geometry, the relationship in equation (2), below, holds:

$$V_2 = V_1 - 2(V_n \cdot V_1) V_n \tag{2}$$

wherein $(V_n \cdot V_1)$ indicates the inner product of the vectors $V_n$ and $V_1$.

Off-axis angle $\theta$ associated with concave mirror 38 is defined as the angle formed by optical axis $A_{34}$ of detection optical system 34 and optical axis $A_{38}$ of concave mirror 38. The latter axis is defined as the line passing through the center $O_{38}$ of concave mirror 38 and the center of curvature $C_{38}$ of concave mirror 38.

Aperture stop 40 and imaging lens 44 are arranged along an axis $\kappa$ inclined by $2\theta$ with respect to optical axis $A_{34}$. Imaging lens 44 includes an optical axis $A_{44}$ which is colinear with the $\kappa$-axis.

Unit vector $V_2$, which indicates the travel direction of light ray $R_2$, is converted to a coordinate along optical axis $A_{44}$. The imaging state of imaging lens 44 is then calculated. Concave mirror 38 is assumed to have a spherical reflecting surface to simplify the explanation, but may, in practice, be aspherical.

With reference to FIGS. 1 and 3, surface 30S has an origin $O_{30}$ at the center thereof, which serves as the origin for the X-Y-Z coordinate system. Another coordinate system, an x-y-z coordinate system, is centered at origin $O_{38}$ of concave mirror 38. The x-axis is the direction parallel to rotation axis $A_{24}$ of tilt stage 24, and the y-axis is orthogonal thereto. Point A is in the X-Y plane, and rays $R_1$ and $R_2$ associated with point A may expressed in terms of the x-y-z coordinate system. The z-axis is in a plane P1 that includes the x-axis and the surface normal to concave mirror surface 38S at center $O_{38}$, passes through center (apex) $O_{38}$ of concave mirror 38, and is perpendicular to the x-axis. The y-axis is perpendicular to the plane that includes the x-axis and z-axis. The coordinates of the center of curvature of concave mirror 38 in the x-y-z coordinate system are at point $C_{38}$ (Rsin $\theta$, 0, Rcos $\theta$). The equation that expresses the location of point B(x, y, z) on reflective surface 38S of concave mirror 38 (x-y-z) is as shown in equation (3), below:

$$(x - R\sin\theta)^2 + y^2 + (z - R\cos\theta)^2 = R^2 \tag{3}$$

The angle $\phi$, formed by the surface normal of surface 30S and the z-axis, i.e., the amount of inclination of tilt stage 24 (or surface 30S), is not present in equation (3) because the location of point B(x,y,z) relative to point A is such that angle $\phi$ is zero. R is the radius of curvature of concave mirror 38, and $\theta$ is the off-axis angle, defined above.

The location of point B, wherein ray $R_1$ originating from point A(X, Y) on surface 30S strikes reflective surface 38S of concave mirror 38, is expressed in the x-y-z coordinate system as shown in equation (4), below:

$$\left( X, Y\cos\varphi, R\sin\theta - \sqrt{R^2 - (X - R\sin\theta)^2 - Y^2\cos^2\varphi} \right) \tag{4}$$

It is preferable to consider normal vector $V_n$ as a unit vector directed from point B to center of curvature $C_{38}$ (i.e., in the direction opposite shown in FIG. 3). Where concave mirror surface 30S is spherical, normal vector $V_n$ is expressed as shown in equation (5), below:

$$V_n = \left( \frac{X - R\sin\theta}{R}, \frac{Y\cos\varphi}{R}, -\frac{\sqrt{R^2 - (X - R\sin\theta)^2 - Y^2\cos^2\varphi}}{R} \right) \quad (5)$$

In apparatus 10 of the present invention, light (e.g., light ray $R_1$) is either reflected or diffracted with a predetermined order from the entire surface 30S of substrate 30. Thus, the direction this light travels (e.g., unit vector $V_1$) is uniform because light beam 84 irradiating surface 30S is nearly parallel (i.e., collimated). Unit vector $V_1$ associated with light ray $R_1$ is parallel to the z-axis, and is expressed as shown in equation (6), below.

$$V_1 = (0, 0, -1) \quad (6)$$

Given the relationships in equations 2, 5 and 6 set forth above, unit vector $V_2$ associated with light ray $R_2$ is expressed as shown in equation (7), below.

$$V_2 = \begin{pmatrix} x, \\ y, \\ z \end{pmatrix} = \begin{pmatrix} -\frac{2(X - R\sin\theta)}{R^2}\sqrt{R^2 - (X - R\sin\theta)^2 - Y^2\cos^2\varphi}, \\ -\frac{2Y\cos\varphi}{R^2}\sqrt{R^2 - (X - R\sin\theta)^2 - Y^2\cos^2\varphi}, \\ \frac{R^2 - 2(X - R\sin\theta)^2 - 2Y^2\cos^2\varphi}{R^2} \end{pmatrix} \quad (7)$$

Unit vector $V_2$ may be expressed in the coordinate system of imaging lens 44, as shown in equation (8), below, if rotated about the y-axis by $2\theta$, and if the $\kappa$-axis is re-expressed in a $\xi$-$\eta$-$\kappa$ orthogonal coordinate system made to coincide with optical axis $A_{44}$.

$$V_2 = \begin{pmatrix} \xi, \\ \eta, \\ \kappa \end{pmatrix} = \begin{pmatrix} -\frac{1}{R^2}\left\{ 2\cos2\theta(X - R\sin\theta)\sqrt{R^2 - (X - R\sin\theta)^2 - Y^2\cos^2\varphi} + \sin2\theta\{R^2 - 2(X - R\sin\theta)^2 - 2Y^2\cos^2\varphi\} \right\}, \\ -\frac{2Y\cos\varphi}{R^2}\sqrt{R^2 - (X - R\sin\theta)^2 - Y^2\cos^2\varphi}, \\ \frac{1}{R^2}\left\{ -2\sin2\theta(X - R\sin\theta)\sqrt{R^2 - (X - R\sin\theta)^2 - Y^2\cos^2\varphi} + \cos2\theta\{R^2 - 2(X - R\sin\theta)^2 - 2Y^2\cos^2\varphi\} \right\} \end{pmatrix} \quad (8)$$

With continuing reference to FIG. 3, unit vector $V_2$ is directed through the center of opening 42 of aperture stop 40 and the light rays (e.g., light ray $R_2$) associated with unit vector $V_2$ are incident imaging lens 44. The latter then forms an image on light receiving surface 48S of image detector 48. Preferably, imaging lens 44 is aberration-free, or nearly so.

With reference again to FIG. 1, it is convenient to consider a u-v coordinate system on light receiving surface 48S of image detector 48. In this u-v coordinate system, the origin is at a point $P_{48}$ where optical axis $A_{44}$ intersects light receiving surface 48S. The u-axis is the direction parallel to the $\xi$-axis, and the v-axis is the direction parallel to the $\eta$-axis. Thus, in the u-v coordinate system, the relationship shown in equation (9) below, holds:

$$u = f \times \xi, \quad v = f \times \eta \quad (9)$$

wherein f is the focal length imaging lens 44 (here, x indicates the scalar product).

With reference to FIG. 3, ray $R_1$ from point $A(X, Y)$ on surface 30S ultimately intersects light receiving surface 48S of image pickup device 48 at a point $D(u,v)$. Accordingly, by making calculations based on the relationships in equations 8 and 9, above, the grid pattern 100 on surface 30S (FIG. 4) becomes a distorted grid pattern image 104 at light receiving surface 48S (FIG. 5).

In practice, imaging lens 44 contains some aberrations. Thus, it is preferable to take the effects of these aberrations into consideration and to calculate the correspondence relationship when ray $R_1$ from point $A(X, Y)$ on surface 30S images to point $D(u, v)$ on light receiving surface 48S. It is preferable to use the results calculated from the aberrations of imaging lens 44 to correct the computational results based on the relationships of equations 8 and 9, above.

Figure 4:
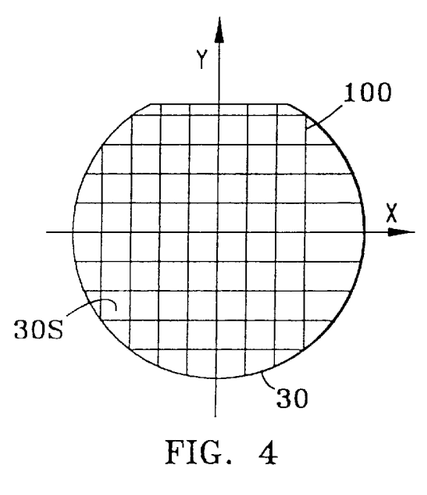
FIG. 4 is a top-down view of a substrate having a periodic pattern formed on the surface thereof.
Figure 5:
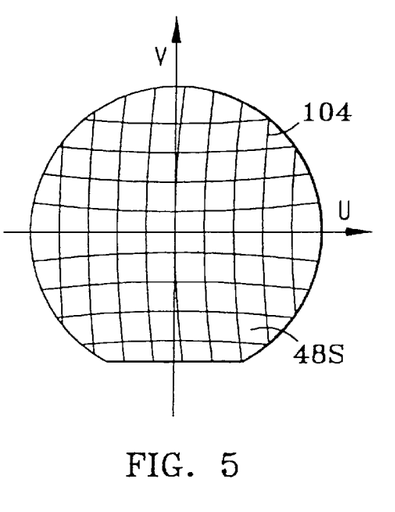
FIG. 5 is a top-down view of the substrate of FIG. 5, showing the distorted substrate surface image formed on the image detector.

Next, performing the above calculations in reverse, image distortion correction unit 62a inside processing system 62 (FIGS. 1 and 2) corrects distortion so that the distorted image of surface 30S (image 104, FIG. 5) formed on light receiving surface 48S changes to the original correct image (image 100, FIG. 4). The inspection of defects and foreign matter is performed by image processing unit 62b based on an algorithm that does not detect as a defect the periodic structure of the pattern (e.g., grid pattern 100) on surface 30S.

The light (e.g., light ray $R_2$) arriving at point $D(u, v)$ is expressed as shown in (10), below, in the $\xi$-$\eta$-$\kappa$ coordinates between concave mirror 38 and imaging lens 44:

$$V_2 = (\xi, \eta, \kappa) = \left( \frac{u}{f}, \frac{v}{f}, \sqrt{1 - \frac{u^2 + v^2}{f^2}} \right) \quad (10)$$

Converting this equation to the x-y-z coordinates results in equation (11) below:

$$V_2 = (x, y, z) = \left( \frac{u}{f}\cos2\theta + \sin2\theta\sqrt{1 - \frac{u^2 + v^2}{f^2}}, \frac{v}{f}, -\frac{u}{f}\sin2\theta + \cos2\theta\sqrt{1 - \frac{u^2 + v^2}{f^2}} \right) \quad (11)$$

With reference to FIG. 3, normal vector $V_1$ is parallel to the z-axis. In other words, the coordinates of reflection point B $(x,y,z)$ when $V_1 = (0, 0, -1)$ is derived from the expression for reflection and from the equation describing reflective surface 38S of concave mirror 38. Accordingly, normal vector $V_n$ at point $B(x, y, z)$ is expressed as shown in equation (12), below:

$$V_n = \frac{\overline{C_{38}B}}{|\overline{C_{38}B}|} = \left( \frac{x - R\sin\theta}{R}, \frac{y}{R}, \frac{z - R\cos\theta}{R} \right) \quad (12)$$

Substituting $V_1$, $V_2$ and $V_n$ above in the expression for reflection and deriving the coordinates of point B $(x, y, z)$ results in equation (13), below:

$$x = R\sin\theta - \frac{R}{\sqrt{2}} \frac{\frac{u}{f}\cos 2\theta + \sin 2\theta \sqrt{1 - \frac{u^2 + v^2}{f^2}}}{\sqrt{1 - \frac{u}{f}\sin 2\theta + \cos 2\theta \sqrt{1 - \frac{u^2 + v^2}{f^2}}}} \quad (13)$$

$$y = -\frac{R}{\sqrt{2}} \frac{\frac{v}{f}}{\sqrt{1 - \frac{u}{f}\sin 2\theta + \cos 2\theta \sqrt{1 - \frac{u^2 + v^2}{f^2}}}}$$

$$z = R\cos\theta - \frac{R}{\sqrt{2}} \sqrt{1 - \frac{u}{f}\sin 2\theta + \cos 2\theta \sqrt{1 - \frac{u^2 + v^2}{f^2}}}$$

Point A (X, Y) from which light ray $R_1$ with unit vector $V_1$ originates, is derived by equation (14) below, based on the coordinate transformation x=X and y=Y$\cos\phi$:

$$X = R\sin\theta - \frac{R}{\sqrt{2}} \frac{\frac{u}{f}\cos 2\theta + \sin 2\theta \sqrt{1 - \frac{u^2 + v^2}{f^2}}}{\sqrt{1 - \frac{u}{f}\sin 2\theta + \cos 2\theta \sqrt{1 - \frac{u^2 + v^2}{f^2}}}} \quad (14)$$

$$Y = -\frac{R}{\sqrt{2}\cos\theta} \frac{\frac{v}{f}}{\sqrt{1 - \frac{u}{f}\sin 2\theta + \cos 2\theta \sqrt{1 - \frac{u^2 + v^2}{f^2}}}}$$

In this manner, image distortion correction unit 62a (FIGS. 1 and 3) performs a computation based on the information from inclination detection apparatus 66 and information from image detector 48, as well from equation (14), above. Image distortion correction unit 62a then outputs an image correction signal to image processing unit 62b. This image correction signal corrects the distortion in the image of surface 30S. Consequently, image processing unit 62b performs image processing that extracts the features of defects on surface 30S from the corrected image. Thus, false detection due to distortion of the image of surface 30S can be prevented, allowing a stable, highly efficient, highly accurate inspection of the substrate surface.

It may be desirable to perform image comparison in image processing unit 62b. In this case, substrate 30 must be aligned with respect to detection optical system 34, since there is distortion in the image formed by the detection optical system. Nevertheless, image distortion correction unit 62a is capable of calculating the image distortion based on the amount of positional offset of the mounting of substrate 30 with respect to detection optical system 34. Thus, by electrically performing offset processing of the image and outputting a corrected signal to image processing unit 62b, the latter can perform the image comparison without aligning substrate 30.

As discussed above, apparatus 10 of FIG. 1 includes tilting apparatus 24 for tilting substrate 30. However, apparatus 10 may be constituted so that the diffracted or reflected light is detected by tilting illumination system IS or detection optical system 34 in accordance with the pitch of the pattern (e.g., pattern 100, FIG. 4) on substrate surface 30S.

In the present invention, it is not necessary to make the inclination direction of substrate 30 orthogonal to the off-axis direction of concave mirror 38. However, it is preferable to do so to keep the correction expression for correcting distortion in the image of substrate surface 30S simplified. If not made orthogonal, it is better to perform calculations after converting the coordinates on substrate 30 to the coordinates in a direction orthogonal thereto.

In the present invention, reflecting surface 38S is preferably spherical. However, surface 38S can also be made paraboloidal or a hyperboloidal by deriving the surface normal and calculating the travel direction of the reflected light, since the previously mentioned reflection surface normal is general and holds for a paraboloidal or a hyperboloidal reflective surface. Generally, reflective surface 38S may be made aspherical. In addition, a plurality of receiving mirrors may also be constituted in detection optical system 34. In this case, the elimination of the effects of image distortion or the correction of image distortion can be achieved by calculating the image distortion due to the plurality of receiving mirrors.

Apparatus 10 of the present invention is applicable to apparatus for inspecting the surface of an object for defects or surface structure generally. It will be appreciated by one skilled in the art that the present invention is also applicable to a variety of applications, such as microscopy. The present invention as applied to microscopy includes an image detector, a focal point detection apparatus that detects the position of the object to be inspected, an alignment apparatus having an image detector to detect the image (image alignment) of the relative position offset of a mask and photosensitive substrate in an exposure apparatus that exposes a mask pattern onto a photosensitive substrate.

What is claimed is:

1. An image detection apparatus comprising:
   a) a tilt stage capable of holding an object and inclining a surface of the object;
   b) an illumination system designed so as to illuminate the surface with light;
   c) a detection optical system to form an image of the surface;
   d) a photoelectric detector, that photoelectrically detects said image;
   e) an inclination detection apparatus in communication with said tilt stage, designed to detect said inclination and to provide an output signal corresponding to said inclination;
   f) an image distortion correction unit, electrically connected to said photoelectric detector and said inclination detection apparatus, designed so as to substantially eliminate said amount of distortion in said image and form a substantially distortion-free image; and
   g) an image processing unit, electrically connected to said image distortion correction unit, that inspects surface in said substantially distortion-free image.

2. An apparatus according to claim 1, wherein said detection optical system includes a mirror which reflects the light from said surface, wherein the mirror does not direct the reflected light back to said surface.

3. An apparatus according to claim 2, wherein said mirror comprises a concave mirror.

4. An apparatus according to claim 3, wherein said detection optical system further comprises, between said concave mirror and said detector:
   a) an aperture stop; and
   b) an imaging lens adjacent said aperture stop.

5. An image detection apparatus according to claim 2, wherein said light from said surface includes at least one of specularly reflected light, scattered light and diffracted light.

6. An apparatus according to claim 5, wherein said illumination system includes a concave mirror.

7. An apparatus according to claim 1, further including a drive apparatus in operable communication with said tilt stage and designed to tilt said tilt stage so as to provide said inclination.

8. An apparatus according to claim 7, further comprising a control unit, electrically connected to said image distortion correction unit and said drive apparatus, that controls said drive apparatus.

9. An apparatus according to claim 1, wherein said image distortion correction unit is electrically connected to said inclination detection apparatus, and wherein said inclination detection apparatus transmits said output signal to said image distortion correction system unit.

10. An image detection apparatus according to claim 1, wherein said light from said surface includes at least one of specularly reflected light, scattered light and diffracted light.

11. An apparatus according to claim 1, wherein said illumination system includes a concave mirror.

12. An apparatus according to claim 2, wherein said illumination system includes a concave mirror.

13. A method of forming a substantially distortion-free image of a surface, the method comprising the steps of:
 a) tilting a stage capable of holding an object and inclining the surface of the object;
 b) illuminating the surface;
 c) collecting light from the surface using a detection optical system;
 d) forming an image of the surface, said image having an amount of distortion;
 e) determining said amount of distortion in said image; and
 f) removing said amount of distortion, as determined in said step e), from said image, thereby forming a substantially distortion-free image.

14. A method according to claim 13, further including the step, after said step f), of inspecting surface in said substantially distortion-free image.

15. A method according to claim 13, further including the steps of detecting and controlling said inclination.

16. A method of forming a substantially distortion-free image of a surface having a surface normal to facilitate identifying surface defects, the method comprising the steps of:
 a) obliquely illuminating the surface;
 b) receiving light from the surface using a detection optical system having a first axis disposed at a first angle with respect to the surface normal;
 c) forming an image of the surface along a second axis forming a second angle with said first axis, said image having an amount of distortion corresponding to said first and second angles;
 d) detecting said image with said amount of distortion and providing a first output signal corresponding to said image with said amount of distortion;
 e) determining said first and second angles and providing a second output signal corresponding to said first and second angles;
 f) inputting said first and second output signals into a distortion correction unit and determining said amount of distortion based on said first and second output signals; and
 g) substantially removing said amount of distortion from said first output signal, thereby creating a third output signal corresponding to a substantially distortion-free image.

17. A method according to claim 16, further comprising the step, after said step g), of:
 a) electronically processing said third output signal so as to identify the surface defects in said substantially distortion-free image.

* * * * *